United States Patent [19]
Heyden

[11] Patent Number: 4,649,915
[45] Date of Patent: Mar. 17, 1987

[54] PLACEMENT MARKING SYSTEM FOR ENDOTRACHEAL TUBES

[76] Inventor: Eugene L. Heyden, S. 627 Bernard No. 8, Spokane, Wash. 99204

[21] Appl. No.: 667,098

[22] Filed: Nov. 1, 1984

[51] Int. Cl.$^4$ ..................... A61M 16/00; A61M 29/00
[52] U.S. Cl. ................................. 128/207.17; 604/100
[58] Field of Search ...................... 128/207.14, 207.15, 128/656, 657, 658, 207.17; 604/79, 96, 100

[56] References Cited

U.S. PATENT DOCUMENTS 1,913,229  6/1933  Bordier ................................. 604/45

FOREIGN PATENT DOCUMENTS 2098485  11/1982  United Kingdom ........... 128/207.15

Primary Examiner—Richard C. Pinkham
Assistant Examiner—Benjamin Layno

[57] ABSTRACT

An endotracheal tube is provided with a placement marker to mark and monitor a correct depth of placement of the endotracheal tube within the breathing pathway. In a preferred embodiment, the forward termination of a marking insert is positioned and retained within a member passage of an endotracheal tube in a spaced relation with a stationary reference structure such as the lips or naris of a patient. Correct tube placement, so distinguished, is thereby ascertainable on a continuing basis by inspection for a continuation of the achieved spaced relation between the forward termination of the marking insert and the stationary reference structure.

26 Claims, 10 Drawing Figures

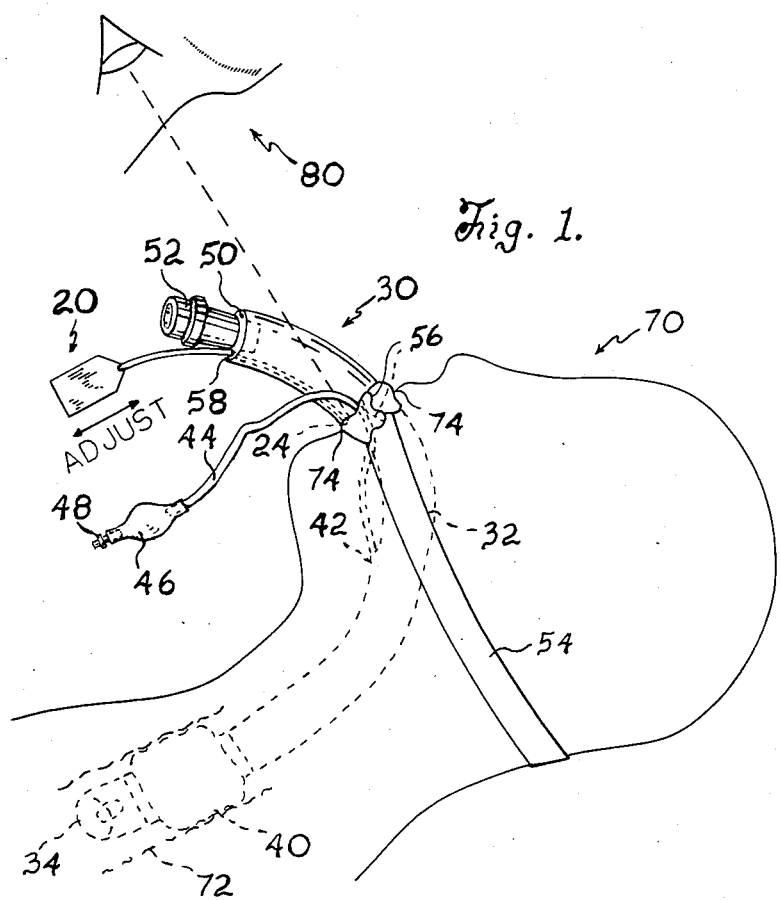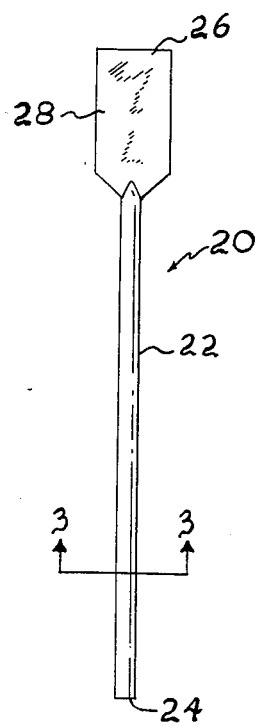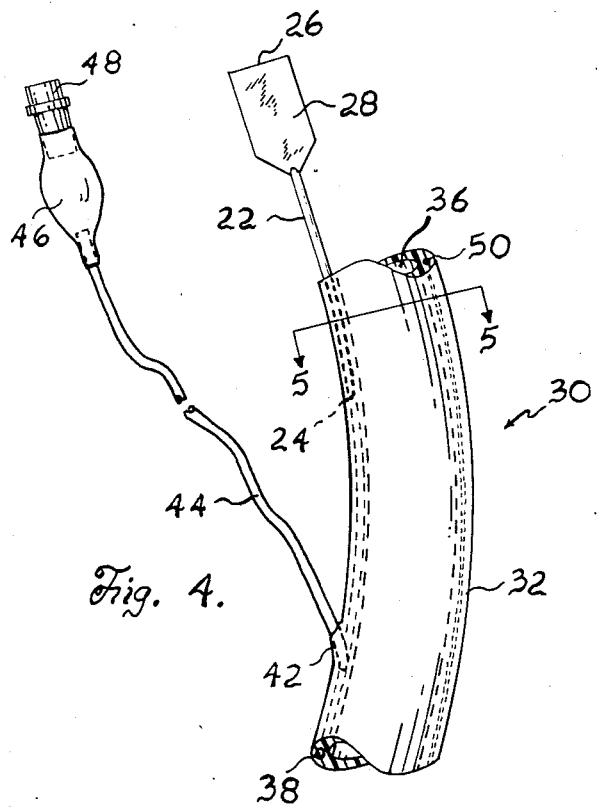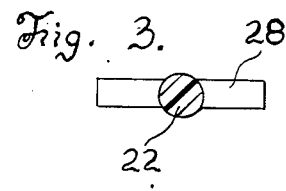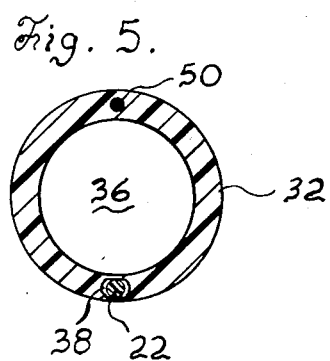

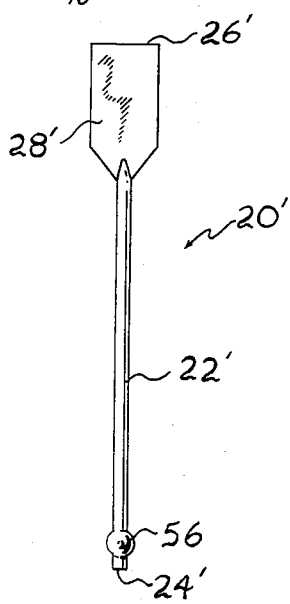
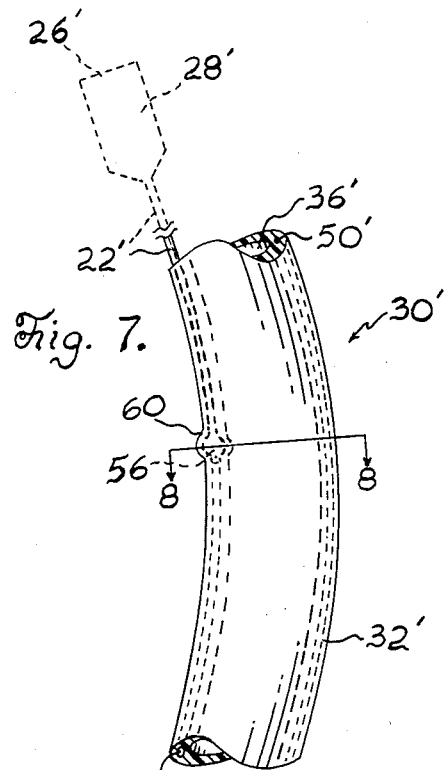
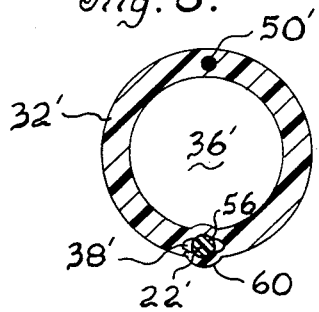
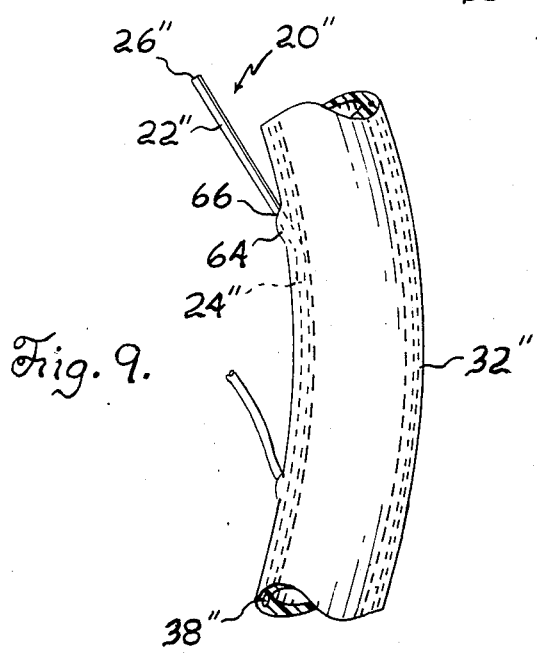
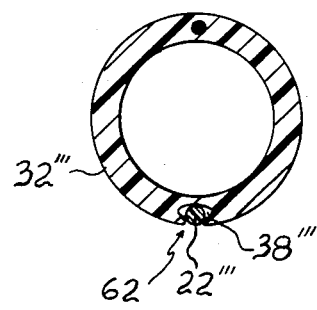

PLACEMENT MARKING SYSTEM FOR ENDOTRACHEAL TUBES

BACKGROUND OF THE INVENTION

This inention relates generally to medical devices for insertion and extended stay within an anatomical pathway, and more particularly to endotracheal tubes wherein the depth of placement within the intubated pathway is of particular concern, necessitating prevention and detection of malposition during use.

Endotracheal tubes are widely known and extensively used in surgical and intensive care settings. Their typical use is to provide respiratory support of patients in physically comprised conditions such as during and following anesthesia or during the course of a serious injury or disease process.

Conventionally, the endotracheal tube comprises an elongated tubular apparatus having a centrally located primary passage and, when placed, has a forward portion and end residing within the trachea and a rearward portion and end residing outside the breathing passage, extending through the mouth or nose. A circumferentially expansible cuff is used in most varieties of endotracheal tubes, residing near its forward end, and is inflated by means of an associating inflation circuit. Beginning with a check valve and test balloon at one end, a fluid conducting element joins a secondary passage provided within the tube wall which in turn is forwardly in fluid communication with the cuff. During intubation the cuff is inflated to provide a seal between the endotracheal tube and the wall of the trachea, thereby allowing oxygen and other gases to pass from the endotracheal tube and into the lungs without escape through the mouth or nose of the patient. Additionally, a radiopaque filament is incorporated within the tube wall, usually the entire length of the tube, and provides for radiographic visualization of the endotracheal tube in reference to associating anatomical landmarks.

Of critical importance to patient welfare is a correct placement of the endotracheal tube forward end and the expansible cuff within the trachea. A particular problem, especially apparent during prolonged tube placement, is the risk of unintentional displacement and malposition of the endotracheal tube. It is the common practice to tape the tube in place immediately upon intubation and to retape the tube as indicated following radiographic determination of its forward portion within the trachea. (A position of 3 to 4 centimeters above the trachea bifurcation is regarded as safe in preventing unwanted contact of the forward end or cuff with the tracheal carina or vocal cords, respectively.) It is an equally common practice to frequently retape the tube as needed to replaced soiled and worn tape, when moving the tube from one side of the mouth to the other side, or when skin integrity is adversely affected by the tape's adhesive surface. Adding to the displacement and malposition risk is the potential that secretions will adversely act on the adhesive surface of the tape as to allow undetected slippage of the endotracheal tube to occur.

A particular problem encountered in the event of endotracheal tube malposition is the problem of disproportionate ventilation of one lung as opposed to the other lung by advancement of the forward end of the endotracheal tube within a mainstem bronchus. Serious sequelae and prolonged and complicated hospitalization may result. An additional radiograph is often taken to verify correct tube readjustment when the position of the endotracheal tube is in question, adding both expense and additional radiation exposure to the list of accompanying problems.

Preceding the present invention, methods used to establish, and identify on an ongoing basis, correct tube placement have proven unsatisfactory. Ink markings manually placed on the endotracheal tube wall adjacent to its point of entrance within the intubated pathway are either hard to place because of interfering tape, or can be rubbed off, covered, or lifted off when retaping. Wall markings printed on the endotracheal tube designating increments of length from a given wall location to the forward end of the tube are also subject to loss and obscurity, and are additionally unsatisfactory in that the correct length is either forgotten or otherwise lost to use by other clinicians. A novel, but equally unsatisfactory method has been employed to mark the entrance point of the tube and consists of placing a suture through the wall of the tube adjacent to its point of entry within the intubated pathway and then circumferentially wrap and tie the suture in place about the tube body. This procedure is costly, time consuming, and often interferes with tape replacement. If not carefully placed, the suture acts to block a suction catheter, endoscope, or the like from passing through the primary passage of the endotracheal tube. All too often the inconvenience and inadequacies of these methods discourage the use of any marking system, underscoring the need for the invention herein described.

SUMMARY OF THE INVENTION

The present invention provides for endotracheal tubes a placement marking system for indicating a correct depth of placement of the endotracheal tube within the intubated pathway. As demonstrated in preferred embodiments, an elongated insert presenting a distinguishing means, such as the forward termination of the insert, is included to a receptive passage acessably defined within the tubular member of the endotracheal tube. The insert is positioned within the passage to achieve a spaced relation between the distinguishing means and a stationary reference means such as the patient's lips or naris. The tubular member provides for the sensory perception of the distinguishing means at a time when the insert is included to the passage. After intubation is accomplished, and at a time when the endotracheal tube is known to extend to a desired depth within the intubated pathway, the marking insert is positioned to reside at a location within the passage. The spaced relation between the distinquishing means and the stationary reference means allows for an inspection for a continuation of the achieved spaced relation to determine a continution of a correct path of placement of the endotracheal tube within the intubated pathway.

BRIEF DESCRIPTION OF THE DRAWINGS

The invention can best be understood in conjunction with the accompanying drawings to which the description of preferred embodiments correspond.

FIG. 1 is a perspective view of an endotracheal tube shown representatively in proper placement within the trachea, illustrating the use of the marking insert according to the present invention.

FIG. 2 is an elevational view of the marking insert of the preferred embodiment.

FIG. 3 is an enlarged cross-sectional view taken on the line 3—3 of FIG. 2.

FIG. 4 is a fragmentary side elevation of a rearward portion of the endotracheal tube of FIG. 1.

FIG. 5 is an enlarged cross-sectional view taken on the line 5—5 of FIG. 4.

FIG. 6 is an elevational view of the marking insert according to an alternative embodiment.

FIG. 7 is a fragmentary side view of a rearward portion of an endotracheal tube similar to FIG. 4, particularly illustrating alternative embodiments of the present invention.

FIG. 8 is an enlarged cross-sectional view taken on the line 8—8 of FIG. 7.

FIG. 9 is a fragmentary side elevation of a rearwardly disposed portion of an endotracheal tube similar to both FIG. 4 and FIG. 7, particularly illustrating the present invention in yet another embodiment.

FIG. 10 is a cross-sectional view of an additional embodiment of the invention as would be taken along a line similar the line 5—5 as taken from FIG. 4, or the line 8—8 taken from FIG. 7.

DETAILED DESCRIPTION OF THE INVENTION

Referring particularly to FIGS. 1, 4, and 5, which illustrates the invention in its preferred embodiment an endotracheal tube 30 of standard construction is shown and normally comprises a cylindrical tube with a curved, semi-rigid tubular member 32 having a forward end 34 and an opposing rearward end. The material used in it's construction is usually of visually transparent plastic material and is somewhat resilient in nature.

The endotracheal tube 30 is adapted for portional insertion to an appropriate depth within the breathing pathway, having a major portion residing therein with its forward portion residing within the trachea 72 and its rearward portion residing outside of the patient 70, as illustrated in FIG. 1. A centrally located primary passage 36, continuous with the entire length of the tubular member 32, comprises the major cross-sectional area of the endotracheal tube 30, as shown in FIG. 5. As a fluid passageway, the primary passage 36 provides for the exchange of respiratory gasses to and from the patient's lungs.

An additional feature common to endotracheal tubes is the expansible cuff 40 which is carried upon the tubular member 32 in the vicinity of the forward end 34. Used to provide a seal with the tracheal wall 72, the cuff 40 prevents the escape of respiratory gasses meant for delivery to the lungs. An inflation circuit is employed to inflate (or deflate) the cuff 40 and comprises a fluid conducting element 44, a formed attachment 42 joining one end of the fluid conducting element 44 with a secondary passage 38 a check valve 48 and pilot balloon 46 assembly carried by the opposing end of the conducting element 44, and fluid communication means (not shown) between the inside of the cuff 40 and the secondary passage 38.

The secondary passage 38, as defined within the inside curve of the tubular member 32, is substantially continuous with the entire length of the endoctracheal tube 30, and is open externally at its origin at the rearward end thereof. The formed attachment 42 provided by the forward insertion of the fluid conducting element 44 a short distance within the secondary passage 38 is generally placed some distance forward from the rearward end 36 of the endotracheal tube, leaving a substantial length of the secondary passage 38 uninvolved with the cuff inflation circuit. This uninvolved length of the secondary passage becomes useful according to a preferred embodiment of the invention, as will be later explained.

Also defined within the tubular member 32 of the endotracheal tube 30 is a radiopaque filament 50 extending the length of the tube along its outside curvature. Its relative position in the endotracheal tube is demonstrated in FIG. 4 and in the cross section in FIG. 5. This filament provides for radiographic visualization of the position of the endotracheal tube, especially its forward end 34, following intubation within the trachea 72.

FIG. 1 shows the endotracheal tube as it would appear when correctly and commonly intubated within a patient. The forward end 34 and cuff 40 are illustrated as being properly positioned within the trachea 72 of the representative patient 70. The tubular member 32 extends outside the patient 70, passing beyond the lips 74, and supports, at its rearward end, a connector 52 for joining to a ventilating device (not shown). The endotracheal tube is held in place by an encircling length of tape 54 passing around the face and neck. The tape ends 56 are securely wrapped around the endotracheal tube at its point of exit from the body to prevent the tube from inadvertently slipping forward or rearward, thus maintaining the cuff 40 and the forward end 34 in a correctly placed position within the trachea 72, which is - so crucial to patient wellbeing.

Endotracheal tubes are improved according to the present invention by the provision of means to mark and monitor for correct tube placement. As previously mentioned, the rearward length of the secondary passage 38 becomes useful, in this regard, according to a preferred embodiment of the invention. For use in connection with this rearward length of the secondary passage 38, a marking insert 20 is adapted for insertion therein through the rearward opening 58 of the secondary passage 38 which exists in the rearward end of the endotracheal tube.

Referring particularly to FIGS. 2 and 3, the marketing insert comprises an elongated, substantially rigid stem 22 having a forward termination 24 and a rearward termination 26. Placed rearwardly is a widened portion defining a handle 28, useful in holding and gripping the device. The marking insert 20 is sufficient in length to pass a substantial distance within the secondary passage 38 and is adapted to fit snugly therein so as to resist unintentional dislodgment. This fitted relationship is particularly evident by close scrutiny of FIGS. 3 and 4. The preferred characteristics of the marking insert 20 are that the material comprising its construction not only be of sufficient strength to resist folding or breakage during insertion but also be visually opaque or colored as to be clearly visible through the transparent tubular member 32 of the endotracheal tube when placed within the secondary passage 38.

It can be readily appreciated that, once intubation is accomplished and correct placement is either estimated or confirmed by a radiograph, of the marking insert 20 can be manually adjusted within the secondary passage 38 to approximate the forward termination 24 thereof with a stationary reference means such as the patient's lips 74. Being visible to the clinician 80 through the transparent tubular member 32, the presence of the forward termination 24 of the marking insert adjacent to the stationary reference means indirectly indicates the correct placement of the forward end 34 and cuff 40 of the endotracheal tube within the trachea 72, and can so indicate on a continuing basis. Should the forward termination of the marking insert be displaced a distance away from the stationary reference means, a degree of tube displacement can subsequently be determined, alerting the clinician of the need of corrective action. It is also to be appreciated that once the position of the endotracheal tube is correct and the position of the marking insert is accordingly placed to mark the area of the tube adjacent to the stationary reference means, detaching the noninserted excess of the marking insert 20 at its point of exit from the secondary passage 38 (phantomly illustrated in FIG. 7) acts, along with frictional forces between insert and passage, to prevent unintentional dislodgment of the marking insert 20 and subsequent displacement of its position-distinguishing forward termination 24.

It is comtemplated, according to the present invention, that in commercial practice the marking insert be separately supplied for use with endotracheal tubes, or supplied either accompanying an endotracheal tube or pre-inserted within its secondary passage. Also contemplated according to the invention is the provision of a passage, secondary in nature with respect to the primary passage and other than a secondary passage provided for cuff inflation purposes, for association with a marking insert.

FIGS. 6, 7, and 8 taken together are useful to illustrate an alternative embodiment of the invention. As in FIG. 2, the marking insert 20' likewise comprises an elongated stem 22', a rearward termination 26', and a rearwardly disposed handle 28' defining a surface for holding and gripping. However, in this embodiment, an enlargement 56 occurs in the stem 22' near its forward termination 24'. The marking insert 20' operates much the same way as the insert of FIG. 2, the exception being that the forward enlargement 56 is adapted to appreciably deform the secondary passage 38' radially outward. This outward deformation 60 of the secondary passage 38' may be used along or used together with the insert's coloration to distinguish the location distinguished by the marking insert 20', making the presence of the forward termination 24' of the marking insert 20' detectable either by sight or by touch.

The features of the endotracheal tube 30' which appear in FIG. 7 and in enlarged cross section in FIG. 8 (from the line 8—8 of FIG. 7) are much the same as in FIGS. 4 and 5. The tubular member 32' likewise provides a primary passage 36', a secondary passage 38', and a radiopaque filament 50'. A fluid conducting element, as seen in FIG. 4, is not incorporated within the secondary passage 38' to illustrate that a secondary passage adapted solely for the purpose of housing a marking insert may be accomplished according to the invention. Such a passage would be necessary in the smaller type of endotracheal tubes which do not incorporate the use of an expansible cuff.

FIG. 9 illustrates an alternative embodiment of both the marking insert and its means for insertion within the secondary passage. The marking insert 20'', like the one illustrated in FIG. 2, comprises an elongated stem 22'', a forward termination 24'', and a rearward termination 26''. (A handle is not herein shown, pointing to its optional nature in the practice of the invention. Accordingly, the rearward portion of the stem 22'' would serve as means for holding and gripping the device.) A radially outward alteration 64, lateral to the secondary passage 38'', is herein shown and is formed by an alternative point of entry of the marking insert to within the secondary passage 38''. This radially outward alteration 64 of the tubular member 32'' could be, in one instance, caused following an act of piercing through the tubular member 32'' by the forward end 24'' of the marking insert 20'', thereby establishing a lateral opening 66 within the secondary passage 38''. Or alternatively, a lateral opening 66 for side entry into the secondary passage 38'', may be pre-formed in the endotracheal tube.

FIG. 10 is a cross-sectional view of yet another embodiment as would be taken from a rearward portion of the endotrachel tube similar to the cross sections taken from the lines 5—5 and 8—8 of previous figures. In this embodiment, the secondary passage 38'''' formed within the tubular member 32'''' of the endotracheal tube is provided with an elongated slit 62 lateral to and leading to the area within the secondary passage 38''''. This slit may extend a part, or substantially the entire length, of the secondary passage 38''''. As in the other embodiments, the secondary passage 38'''' still acts to receive and retain a marking insert stem 22''', yet the elongated slit 62 provides an opening for access to the secondary passage 38'''' along any of several points along the length thereof. Also, visualization of the marking insert may, in this manner, be made directly instead of through the tubular member of the endotracheal tube.

As can be readily understood from the foregoing, the practice of the invention may be according to various embodiments.

Although described in relation to endotracheal tubes, other medical catheters, and naso-gastric devices could be similarly improved and benefited by application of the present invention.

In keeping with both the foregoing description of the invention and the intent thereof, what is claimed as exclusive property or privilege is:

In keeping with both the foregoing description of the invention and the intent thereof, what is claimed as exclusive property or privilege is:

1. In a tubular medical apparatus comprising an elongated tubular member presenting a longitudinally extending central axis and intended for residing portionally inserted within an anatomical pathway, wherein said tubular member includes a forward portion and forward end adapted for insertion to within a range of depths within said anatomical pathway, and wherein said tubular member also includes a rearward portion and rearward end for residing a distance outside said anatomical pathway, the improvement of a placement marking system for indicating a correct depth of placement of said tubular member within said anatomical pathway, said marking system comprising:

an elongated guide means integral with and extending along said tubular member, said guide means residing in the rearward portion of said tubular member and extending forwardly in length a distance sufficient to provide a range of marking sites with respect to an intended stationary reference means appropriate for referencing, said stationary reference means being distinct from said apparatus and stationary with respect to a range of localities within said anatomical pathway, said guide means presenting a longitudinally extending central axis, having a receptive interior, and of a character suitable for guiding and positionally retaining an insert means intended for association therewith;

insert means of longitudinal extent adapted for inclusion within said guide means by the performance of an inclusionary step, and also adapted for directional travel within said guide means when influenced to achieve a position therein, said insert means providing a distinguishing means for residing at least partially within said guide means and of a character allowable by said tubular member for perceptually distinguishing a location within said range of marking sites and with respect to said stationary reference means, said distinguishing means to be guided by said guide means to a position for marking a location within said range of marking sites to indicate a correct depth of placement of said tubular member within said anatomical pathway, said insert means to be manually positioned within said guide means to relate said distinguishing means and said stationary reference means in a spaced relation at a time when said tubular member extends to a desired depth within said anatomical pathway; and means provided by said tubular member allowing sensory perception of said distinguishing means during a time when said insert means is included within said guide means;

whereby, said insert means is controllably positionable when included within said guide means to relate said distinguishing means in suitable spaced relation with said stationary reference means and a wall portion of said tubular member suitably spaced related with the same, so that said distinguishing means and said stationary reference means can relate and indicate on a continuing basis a correct or incorrect depth of placement of said tubular member within said body pathway by allowing for an inspection for a respective continuation of, or a substantial degree of departure from, the achieved spaced relation between said distinguishing means and said stationary reference means.

2. The placement marking system as characterized by claim 1, wherein said guide means is adjacent to the exterior of said tubular member, said guide means being formed recessively therein; and said tubular member provides and entry means allowing entry by said inset means to achieve a position within said guide means.

3. The placement marking system as characterized by claim 2, wherein said entry means comprises said guide means being exteriorly open by means of an opening defined by said tubular member.

4. The placement marking system as characterized by claim 3, wherein said opening is defined at the rearward end of said tubular member.

5. The placement marking system as characterized by claim 2, wherein said entry means is lateral to the central axis of said guide means, said entry means provided by the rearward portion of said tubular member.

6. The placement marking system as characterized by claim 5, wherein said entry means comprises the rearward portion of said tubular member providing an opening leading to the interior of said guide means.

7. The placement marking system as characterized by claim 5, wherein said entry means comprises said tubular member yieldable to forceful penetration by said insert means to gain entry to within said guide means.

8. The placement marking system as characterized by claim 5, wherein said entry means comprises an elongated slit provided together with said guide means by said tubular member, said slit included in the rearward portion of said tubular member.

9. The placement marking system as characterized by claim 8, wherein said slit extends in length a substantial distance toward the forward end of said tubular member.

10. The placement marking system as characterized by claim 2, wherein said means allowing sensory perception of said distinguishing means comprises said tubular member having deformable properties; and said distinguishing means comprises a deforming means provided by said insert means, said deforming means provided to deform said guide means radially outward for providing an outward deformation in said tubular member suitable for sensory perception and for extablishing a spaced relation with said stationary reference means.

11. The placement marking system as characterized by claim 2, wherein said guide means comprises a centrally open passage formed within said tubular member.

12. The placement marking system as characterized by claim 11, further comprising a fluid passageeway centrally located within said tubular member, an expansible cuff carried in the vicinity of said forward end, and cuff inflation means, said cuff inflation means provided in part by said passage, said passage being substantially continuous with the longitudinal extent of said tubular member and having a length thereof for association with said insert means, said associating length uninvolved with the inflation of said cuff.

13. The placement marking system as characterized by claim 1, wherein said guide means is substantially continuous with the longitudinal extent of said tubular member.

14. The placement marking system as characterized by claim 1, wherein said insert means comprises an elongated and substantially rigid stem presenting a longitudinal axis and including a forward termination and a rearward termination, said stem adapted for at least partial inclusion within said guide means, and also adapted to frictionally relate therewith.

15. The placement marking system as characterized by claim 14, further comprising a substantially lateral projection depending from said stem and extending a distance away from the longitudinal axis thereof, said lateral projection defining a member inviting manual contact during the positioning of said stem.

16. The placement marking system as characterized by claim 1, wherein said insert means presents a forward termination, and said distinguishing means includes the forward termination of said insert means.

17. The placement marking system as characterized by claim 1, wherein said means allowing sensory perception of said distinguishing means allows for visualization of said distinguishing means; and said distinguishing means is visually appreciable when residing within said guide means.

18. The placement marking system as characterized by claim 17, wherein said means allowing the sensory perception of said distinguishing means comprises said tubular member having visually transparent properties.

19. The placement marking system as characterized by claim 17, wherein said means allowing sensory perception of said distinguishing means includes an elongated slit presented by said tubular member and residing within said range of marking sites, said slit allowing communication between the interior of said guide means and a region outside said guide means, said slit allowing at least a portion of said discrimination means to be unconfined by said tubular member and visually appreciable at a time when said insert means is included within said guide means.

20. A method of marking a correct depth of placement of an elongated tubular medical apparatus as it resides portionally inserted within an anatomical pathway and to a depth within a range of depths therein, wherein said apparatus includes a tubular member of longitudinal extent, said tubular member including a forward portion and forward end adapted for insertion within said anatomical pathway, including a rearward portion and rearward end for residing a distance outside said anatomical pathway, and also including an inclusionable area of longitudinal extent defined therein and residing within said rearwad portion, said inclusionable area extending in length forwardly a substantial distance toward said forward end and suitable for positionally retaining an insert means at any of several locations and allowing sensory perception of a distinguishing means provided by an insert means, said method comprising the steps of:

locating the entrance point where said tubular member enters said anatomical pathway; and said distinguishing means residing at least partially within said inclusionable area and positioned to relate said distinguishing means in a spaced relation with said entrance point at a time when said tubular member is at a correct depth within said anatomical pathway, whereby an inspection for a continuation of an achieved spaced relation between said distinguishing means and said entrance point, or a substantial departure from an achieved spaced relation between the same causes by a displacement of said tubular member, serves to indicate a respective correct or incorrect depth of placement of said tubular member within said body pathway.

21. A tubular medical apparatus comprising:

an elongated tubular member for residing portionally inserted within an anatomical pathway, said tubular member including a forward portion and forward end adapted for insertion to within a range of depths within said anatomical pathway, and also including a rearward portion and rearward end for residing a distance outside said anatomical pathway;

an elongated guide means integral with and extending along said tubular member from the vicinity of said rearward end a substantial distance toward said forward end, said guide means presenting a longitudinally extending central axis and a receptive interior;

insert means received within said guide means and slidably movable within the same, said insert means of longitudinal extent, substantially rigid in character, and including a distinguishing means residing at least partially within said guide means and suitable for distinguishing a location and marking a correct depth of placement of said tubular member within said anatomical pathway, said guide means adapted to retain said insert means, said insert means adapted for sustained positioning within said guide means; and means provided by said tubular member for allowing sensory perception of said distinguishing means;

whereby, at a time when said tubular member is residing portionally inserted within said guide means, said insert means is adjustable to achieve a spaced relation between said distinguishing means and a stationary reference means appropriate for referencing, said stationary reference means distinct from said apparatus and stationary with respect to a range of localities within said anatomical pathway, so that a continuation of the achieved spaced relation between said insert means and said guide means serves to indicate a continuation of a correct depth of placement of said tubular member within said anatomical pathway, and a substantial departure from the achieved spaced relation between said distinguishing means and said stationary reference means caused by a displacement of said tubular member serves to indicate a malposition of said tubular member within said anatomical pathway.

22. The apparatus of claim 21, wherein said guide means is recessively formed within said tubular member and extends a substantial distance within and along the same.

23. The apparatus of claim 23, wherein said guide means comprises a passage formed within said tubular member;

wherein said distinguishing means is visually appreciable; and said means allowing sensory perception of said distinguishing means comprises said tubular member having visually transparent properties.

24. The apparatus of claim 22, wherein said guide means comprises a passage formed within said tubular member;

wherein said means allowing sensory perception of said distinguishing means comprises said tubular member having deformable properties; and said distinguishing means comprises an enlargement integral to said insert means and adapted to deform said tubular member radially outward for providing an appreciable outward deformation in said tubular member.

25. The apparatus of claim 22, wherein said guide means is formed by said tubular member to include therewith a longitudinally extending slit forming communication between the interior of said guide means and a region outside the same; and said means allowing sensory perception of said distinguishing means includes said slit, said slit allowing at least a portion of said distinguishing means to be structurally unconfined by said tubular member.

26. The apparatus of claim 21, wherein said insert means is also adapted to extend a distance outside said guide means.

* * * * *

UNITED STATES PATENT AND TRADEMARK OFFICE
CERTIFICATE OF CORRECTION

PATENT NO. : 4,649,915

DATED : Mar. 17, 1987

INVENTOR(S) : Eugene L. Heyden

It is certified that error appears in the above-identified patent and that said Letters Patent are hereby corrected as shown below:

Col. 1, line 6, "inention" should be --invention.
Col. 3, line 27, place a comma after "embodiment".
Col. 3, line 55, place a comma after "38".
Col. 3, line 68, delete "36".
Col. 4, line 28, after "72" delete ", which".
Col. 4, line 29, delete "is".
Col. 4, line 60, delete "of".
Col. 5, line 18, "comtemplated" should be --contemplated--.
Col. 6, delete lines 39, 40 and 41.
Col. 7, line 35, "body" should be --anatomical--.
Col. 8, line 22, "passageeway" should be --passageway--.
Col. 9, lines 25 and 26 should read --positioning within said inclusionable area an insert means having a distinguishing means, said distinguishing means residing at least partially within said inclusionable area and allowable by said tubular member for distinguishing said location and for marking a correct depth of placement of said tubular member within said anatomical pathway, said insert means positioned to--.

Signed and Sealed this

Eleventh Day of August, 1987

*Attest:*

DONALD J. QUIGG

*Attesting Officer*  *Commissioner of Patents and Trademarks*